US011578308B2

(12) United States Patent
Lauster et al.

(10) Patent No.: US 11,578,308 B2
(45) Date of Patent: Feb. 14, 2023

(54) METHOD OF PREPARING AN ARTIFICIAL TOOTH PRIMORDIUM IN VITRO AND ARTIFICIAL TOOTH PRIMORDIUM DERIVED THEREFROM

(71) Applicant: TECHNISCHE UNIVERSITAET BERLIN, Berlin (DE)

(72) Inventors: Roland Lauster, Berlin (DE); Uwe Marx, Spreehagen (DE); Jennifer Binder, Berlin (DE); Mark Rosowski, Berlin (DE)

(73) Assignee: TECHNISCHE UNIVERSITAET BERLIN, Berlin (DE)

( * ) Notice: Subject to any disclaimer, the term of this patent is extended or adjusted under 35 U.S.C. 154(b) by 272 days.

(21) Appl. No.: 16/251,560

(22) Filed: Jan. 18, 2019

(65) Prior Publication Data

US 2019/0185815 A1 Jun. 20, 2019

Related U.S. Application Data

(62) Division of application No. 14/381,660, filed as application No. PCT/EP2013/053361 on Feb. 20, 2013, now abandoned.

(30) Foreign Application Priority Data

Feb. 29, 2012 (EP) .................................. 12157470

(51) Int. Cl.
*A61L 27/38* (2006.01)
*C12N 5/077* (2010.01)
(Continued)

(52) U.S. Cl.
CPC ............ *C12N 5/0654* (2013.01); *A61K 35/32* (2013.01); *A61L 27/3804* (2013.01);
(Continued)

(58) Field of Classification Search
CPC ................ C12N 5/0654; C12N 5/0664; C12N 2502/094; C12N 2506/1361;
(Continued)

(56) References Cited

U.S. PATENT DOCUMENTS 7,588,936 B2  9/2009  Sharpe
2007/0231275 A1* 10/2007 Ueda .......................... A61P 1/02
424/50

(Continued)

FOREIGN PATENT DOCUMENTS

EP    1905459    4/2008
EP    2130909    12/2009
(Continued)

OTHER PUBLICATIONS

Yamamoto et al., Analysis of tooth formation by reaggregated dental mesenchyme from mouse embryo, Journal of Electron Microscopy 52(6): 559-566 (2003) (Year: 2003).*

(Continued)

*Primary Examiner* — Louise W Humphrey
*Assistant Examiner* — Anjali Ajit Hirani
(74) *Attorney, Agent, or Firm* — Fox Rothschild LLP (57) ABSTRACT

The present invention is directed to a method of preparing an artificial tooth primordium in vitro, comprising the steps: a) providing isolated mesenchymal dental pulp cells; and b) culturing the mesenchymal dental pulp cells under non-adherent conditions to form a cell aggregate representing an artificial tooth primordium; as well as to an artificial tooth primordium derived therefrom.

9 Claims, 4 Drawing Sheets

(51) Int. Cl.
| | |
|---|---|
| *C12N 5/0775* | (2010.01) |
| *A61K 35/32* | (2015.01) |
| *G01N 33/50* | (2006.01) |
| *G01N 33/68* | (2006.01) |

(52) U.S. Cl.
CPC ....... *A61L 27/3821* (2013.01); *A61L 27/3865* (2013.01); *C12N 5/0664* (2013.01); *G01N 33/5044* (2013.01); *G01N 33/6887* (2013.01); *A61L 2430/12* (2013.01); *C12N 2502/094* (2013.01); *C12N 2506/1361* (2013.01); *C12N 2513/00* (2013.01)

(58) Field of Classification Search
CPC . C12N 2513/00; A61K 35/32; A61L 27/3804; A61L 27/3821; A61L 27/3865; A61L 2430/12; A61L 27/38; G01N 33/5044; G01N 33/6887; G01N 33/50
See application file for complete search history.

(56) References Cited

U.S. PATENT DOCUMENTS

| | | |
|---|---|---|
| 2010/0047211 A1 | 2/2010 | Mcniece |
| 2010/0093080 A1* | 4/2010 | Yamaki ............... A61L 27/3865 435/346 |
| 2010/0119997 A1* | 5/2010 | Tsuji ...................... A61P 1/02 433/215 |
| 2010/0172951 A1 | 7/2010 | Wasielewski |
| 2011/0158962 A1 | 6/2011 | Ferro |
| 2011/0212414 A1 | 9/2011 | Tsuji et al. |

FOREIGN PATENT DOCUMENTS

| | | |
|---|---|---|
| EP | 2322133 | 5/2011 |
| WO | 2002/07679 | 1/2002 |
| WO | 0207679 | 1/2002 |
| WO | 2003066840 | 8/2003 |
| WO | 2005051436 | 8/2008 |
| WO | 2009/146911 | 12/2009 |

OTHER PUBLICATIONS

Gronthos et al., Postnatal human dental pulp stem cells (DPSCs) in vitro and in vivo, PNAS, Dec. 5, 2000, vol. 97, No. 25, 13625-13630 (Year: 2000).*
Baraniak et al., Scaffold-free culture of mesenchymal stem cell spheroids in suspension preserves multilineage potential, Cell Tissue Res, 347:701-711, Aug. 11, 2011 (Year: 2011).*
Zhang et al., Three-Dimensional Spheroid Culture of Human Gingiva-Derived Mesenchymal Stem Cells Enhances Mitigation of Chemotherapy-Induced Oral Mucositis, Stem Cells and Development, vol. 21, No. 6, Jun. 21, 2011 (Year: 2011).*
Iohara et al., Dentin Regeneration by Dental Pulp Stem Cell Therapy with Recombinant Human Bone Morphogenetic Protein 2, J Dent Res 83(8):590-595, 2004 (Year: 2004).*
Hildebrandt et al., A scaffold-free in vitro model for osteogenesis of human mesenchymal stem cells, Tissue and Cell 43 (2011) 91-100 (Year: 2011).*
PHEMA, poly(2-hydroxyethyl methacrylate), Chempilots, Webpage, 2022 (Year: 2022).*
Yip et al., A multicellular 3D heterospheroid model of liver tumor and stromal cells in collagen gel for anti-cancer drug testing, Biochemical and Biophysical Research Communications 433 (2013) 327-332.
Pipette tips, Lab Unlimited Pipette tips catalog, 2018.
Anonymous: Internet Article (Thermo Scientific product literature), Jan. 1, 2009 (Jan. 1, 2009), XP55037827, Retrieved from the Internet: URL:http://www.tslaborhu/depo/Inkubator/NUNC Solutions for cell culture growth and analysis.pdf [retrieved on Sep. 11, 2012].
N A Dorfman et al: "Susceptibility of Adherent Versus Suspension Target Cells Derived From Adherent Tissue Culture Lines to Cell-Mediated Cytotoxicity in Rapid 51Cr-Release Assays", Journal of Immunological Methods, Jan. 1, 1980 (Jan. 1, 1980), vol. 32 pp. 127-139.
Christensen et al: "An Immunocytochemical Study of the Innervation of Developing Human Fetal Teeth Using Protein Gene Product 9.5 (PGP 9.5)", Archs oral Biol. vol. 38, No. 12, pp. 1113-1120, 1993.
Lechguer et al: "Vascularization of Engineered Teeth", J Dent Res 87(12):1138-1143, 2008.
Giamieri et al: "EMT markers in lung adenocarcinoma pleural effusion spheroid cells", Journal of Cellular Physiology, Accepted Nov. 27, 2012.
Smith et al: "Inhibition of Activin/Nodal signaling promotes specification of human embryonic stem cells into neuroectoderm", Developmental Biology 313 (2008) 107-117.
Yu et al: "RNA sequencing of pancreatic circulating tumour cells implicates WNT signalling in metastasis", Nature vol. 487, Jul. 26, 2012. pp. 510-513, plus supplementary material online.
ThermoFisher, Webpage, 2016.
Tooth, Tooth Development, Presentation, 2016.
International Search Report dated Mar. 11, 2013 in International Application No. PCT/EP2013/053361. (3 pages).

* cited by examiner

METHOD OF PREPARING AN ARTIFICIAL TOOTH PRIMORDIUM IN VITRO AND ARTIFICIAL TOOTH PRIMORDIUM DERIVED THEREFROM

CROSS-REFERENCE TO RELATED APPLICATIONS

This application is a divisional patent application of U.S. patent application Ser. No. 14/381,660 filed Aug. 28, 2014, which is a § 371 national stage entry of International Application No. PCT/EP2013/053361, filed Feb. 20, 2013, which claims priority to European Application No. 12157470.1 filed Feb. 29, 2012, the entireties of which are hereby incorporated by reference.

BACKGROUND OF THE INVENTION

Dental care is the best way of maintaining healthy denture. However, even under optimal dental care impairment, destruction or loss of teeth can occur. Such impairment, destruction or loss of teeth may be e.g. disease-related, hormone-related, therapy-related or a consequence of an accident. Nowadays, in such a case dental implants are used which usually are formed of materials comprising metal (e.g. titan), ceramics and/or composites. These implant techniques are highly sophisticated and from a medical and cosmetic point of view achieve already high levels. However, these tooth replacement therapies require a significant surgical procedure and, eventually, laborious follow-up care. In addition, these synthetic implants do not meet all demands on a tooth like e.g. an "absorption" by the natural periodontal ligament which fixes the tooth within the jawbone.

Thus, it is an aim in the field of regenerative medicine to provide means which allow the production or induction of tissue or organs that equal the respective naturally occurring tissues and organs in function and morphology. One approach is the provision of artificial tissue or organs that can be used in tooth regeneration in vitro and/or in vivo. Such artificial tissue comprises tissue that has been produced by biotechnological means.

Apart from the problem of providing a tissue that is capable of forming a tooth in vivo that sufficiently equals naturally occurring teeth in function and morphology, it is another object to provide a tissue that can be manufactured without the need of embryonic stem cells and that makes use of cells originating from the patient to be treated.

In numerous approaches first attempts and progress have been made towards tissue that serves this purpose. Examples of such approaches are described in EP 1 905 459 A1, EP 2 130 909 A1, US 2007/0231275 A1, US 2011/0212414 and WO 2005/051436 A2. However, in most of these approaches embryonic cells are used, the cells are cultured under non-physiological adherent culture conditions and require the presence of a synthetic scaffold or carrier.

Thus, it is an option of the present invention to provide means to overcome one or more problems of the prior art. In particular it is an option of the invention to provide an improved method of preparing an artificial tooth primordium in vitro, which can be performed with non-embryonic primary cells.

DISCLOSURE OF THE INVENTION

The present invention relates to a method of preparing an artificial tooth primordium in vitro, comprising the steps of:

a) providing isolated mesenchymal dental pulp cells; and
b) culturing the mesenchymal dental pulp cells under non-adherent conditions to form a cell aggregate representing an artificial tooth primordium.

It has surprisingly been found that isolated mesenchymal dental pulp cells are capable of forming a three dimensional cell aggregate representing an artificial tooth primordium without influence of embryonic epithelial cells. This effect is achieved by culturing the mesenchymal dental pulp cells under non-adherent conditions. It could be shown that under such non-adherent culture conditions the mesenchymal dental pulp cells arrange freely to each other and condense to a cell aggregate which exhibits expression of markers specific for tooth germ structures and which are therefore denoted tooth primordium.

In the following, different aspects of the invention are provided in more detail. Each aspect so defined may be combined with any other aspect or aspects unless clearly stated to the contrary. In particular, any feature indicated as being preferred or advantageous may be combined with any other feature or features indicated as being part of the invention or being indicated as being preferred or advantageous.

The method of the present invention is directed to the preparation of an artificial tooth primordium in vitro. An artificial tooth primordium is a tooth primordium that has been prepared and assembled de novo and in vitro.

For the purpose of the present invention the term "tooth primordium" refers to a functional cell aggregate of one or more than one cell type that exhibits at least one function that is specific for dental tissue or a functional tooth germ. Preferably the tooth primordium of the present invention exhibits the majority or essentially all organ or tissue functions of a dental tissue or a functional tooth germ or tooth. In particular the tooth primordium of the present invention may behave like a functional inductive tooth germ and is capable of inducing tooth organ development or development of a complete tooth in vitro and/or in vivo. The tooth primordium of the present invention may be characterized by elevated expression of marker genes or proteins that are associated with development or differentiation of dental tissue. Preferably the tooth primordium of the present invention may be characterized by elevated expression of BMP4, HGF, PAX9, MSX1, Collagen type I, DSPP and/or predentin compared to isolated mesenchymal dental pulp cells immediately prior to subjecting to non-adherent culturing conditions. Furthermore, a basement membrane formation, mainly characterized by Collagen type IV expression, may occur in the aggregate. Aggregate formation and culturing conditions may lead to a mineralization of the resulting tissue.

The artificial tooth primordium of the present invention is formed by a method of the present invention. The artificial tooth primordium may exhibit a cell aggregate with a substantially spherical shape and with an average diameter of 0.3 mm to 2 mm, preferably with an average diameter of 0.5 mm to 1.5 mm. The artificial tooth primordium may comprise a cell aggregate comprising an inner core formed of mesenchymal dental pulp cells and an outer layer formed of epithelial cells whereas the epithelial cells may invaginate the inner core at later points in time of co-culturing. Invagination of the cells of epithelial origin may lead to a ameloblastic differentiation of these cells. This differentiation may be characterized by the morphological appearance (columnar arrangement) as well as by elevated expression of ameloblast marker genes or proteins (e.g. BMP7, SHH and/or amelogenin). The artificial tooth primordium of the invention is free of any artificial biological or non-biological scaffold or carrier which does not originate from the cells used in the production of said artificial tooth primordium. The artificial tooth primordium of the invention preferably consists of the cell aggregate formed by a method of the invention, wherein the method has been conducted without the use of any artificial biological or non-biological scaffold or carrier which does not originate from the cells used in said method.

In the method of the invention, isolated mesenchymal dental pulp cells are used. The term "isolated" means that the mesenchymal dental pulp cells are cells that have been isolated from a natural source or progeny thereof which e.g. has been derived by cell proliferation. The mesenchymal dental pulp cells used are preferably derived from dental pulp tissue of a donor tooth or tissue. Preferably, the mesenchymal dental pulp cells are primary cells which have not been transformed or immortalized. These cells may be characterized by positivity for CD90, CD73, CD44, CD29 and HLA I and negativity for CD34 and CD45. They exhibit a spindle-shaped morphology in 2D culture and adhere to plastic. In particular, the mesenchymal dental pulp cells may comprise or consist of adult mesenchymal dental pulp cells. Such adult mesenchymal dental pulp cells are derived from non-embryonic dental pulp tissue of a donor tooth or tissue. The mesenchymal dental pulp cells can be derived from dental pulp tissue of any donor tooth or tissue that has been differentiated to comprise dental pulp tissue. Preferably the mesenchymal dental pulp cells are derived from dental pulp tissue of a tooth, more preferably from a third molar of a donor. The mesenchymal dental pulp cells used in the method of the invention are preferably human dental pulp cells. Human mesenchymal dental pulp cells are derived from dental pulp tissue of human origin.

In the method of the invention, the mesenchymal dental pulp cells can be subjected to culturing under non-adherent conditions at any stage after isolation. However, the formation of cell aggregates is further enhanced if the mesenchymal dental pulp cells have undergone at least some culturing under adherent 2D monolayer conditions. Preferably, the mesenchymal dental pulp cells have been cultured in 2D monolayer culture for at least 1 passage prior to subjecting to culturing under non-adherent conditions. A high efficiency in formation of cell aggregates is maintained over a broad spectrum of passages. However, it has been found that best results are achieved if the mesenchymal dental pulp cells have been cultured in 2D monolayer culture for at least 1 passage and not more than 15 passages. Preferably the mesenchymal dental pulp cells are subjected to non-adherent culture after culture in 2D monolayer for at least 2 passages and not more than 8 passages after isolation.

In the method of the invention, after provision of the isolated mesenchymal dental pulp cells, the mesenchymal dental pulp cells are subjected to non-adherent culture conditions to form cell aggregates.

The formation of cell aggregates is particularly effective if the mesenchymal dental pulp cells are subjected to non-adherent culture conditions at a certain concentration. If the concentration is too low, cells have only rarely contact to each other and condensation to cell aggregates is less effective. On the other hand, if the concentration of mesenchymal dental pulp cells is too high, cells are less flexible or mobile and, thus, the formation of cell aggregates is less effective. Preferably, the mesenchymal dental pulp cells are subjected to non-adherent culture conditions at a concentration of $5\times10^4$ to $5\times10^7$ per ml. Even better results are achieved if the mesenchymal dental pulp cells are subjected to non-adherent culture conditions at a concentration of $1\times10^5$ to $1\times10^7$ per ml, preferably of $5\times10^5$ to $5\times10^6$ per ml, and most preferably of $9\times10^5$ to 1, $1\times10^6$ per ml.

In the method of the invention, the isolated mesenchymal dental pulp cells are cultured under non-adherent culture conditions. This means that mesenchymal dental pulp cells are cultured under conditions wherein the cells do not adopt a flattened, spread-out shape indicating strong attachment and adherence to the culture surface. Preferably the mesenchymal dental pulp cells remain rounded directly after seeding and, if at all, only weakly associated with the culture surface. Appropriate means for non-adherent cell culture are well known in the art. Non-adherent culture conditions may comprise culture of the mesenchymal dental pulp cells in culture vessels with a culture surface that does not support adherence of the mesenchymal dental pulp cells. E.g. culture vessels with culture surfaces exhibiting ultra-low cell attachment can be used. For that purpose culture vessels with a neutral or positively charged culture surface may be used. Preferably, the culture surface may be coated by a layer of a material which further reduces interaction of the mesenchymal dental pulp cells and the culture surface. The culture surface may be covered with a hydrophilic hydrogel.

It appears that under non-adherent culture conditions, the mesenchymal dental pulp cells associate and condense to cell aggregates rather quickly. Already after 24 hours of non-adherent cell culture, the mesenchymal dental pulp cells aggregated into one large complex.

However, in order to prepare cell aggregates that represent artificial tooth primordial with progressed development, differentiation and/or function, it is beneficial to conduct non-adherent culturing for a period of time that exceeds 24 hours. In the method of the invention, the mesenchymal dental pulp cells may be cultured under non-adherent conditions for at least 48 hours, preferably for at least 72 hours, more preferably for at least 2 weeks, even more preferably for at least 4 weeks, most preferably for at least 8 weeks. Thus, the mesenchymal dental pulp cells may be cultured under non-adherent conditions for 48 hours to 10 weeks, preferably for 1 week to 9 weeks, more preferably for 4 weeks to 8 weeks.

In the method of the invention, the mesenchymal dental pulp cells are preferably cultured under non-adherent conditions at least until a cell aggregate is formed which exhibits a rounded shape with an average diameter of 0.3 mm to 2 mm, more preferably with an average diameter of 0.5 mm to 1.5 mm.

The suitability of the artificial tooth primordium generated by the method of the present invention is dependent on its ability to induce or provide differentiated dental tissue. Thus, it is preferred to culture the isolated mesenchymal dental pulp cells under non-adherent conditions until the resulting cell aggregate starts to exhibit properties and/or functions of partially or fully differentiated dental tissue. The progression in differentiation can be monitored by the relative expression of respective marker genes, proteins or structures. Preferably, the isolated mesenchymal dental pulp cells are cultured under non-adherent conditions at least until the cell aggregate formed exhibits upregulated expression of BMP4, HGF, PAX9, MSX1 Collagen type I, DSPP and/or predentin compared to isolated mesenchymal dental pulp cells immediately prior to subjecting to non-adherent culturing conditions. Preferably, the formed aggregate exhibits characteristics of the so called cap stage of tooth development with respect to morphology and gene expression. Relative expression of genes can easily be determined by well known methods like e.g. quantitative or semiquantitative RT-PCR, Transcriptome Sequencing (RNA-seq) or Northern blotting. Relative expression of proteins can also be determined by well known methods like e.g. Western blotting, Suspension Array Technology and ELISA techniques. Localization of differential expression of proteins can be determined by in sit hybridization and/or immunohistochemistry.

One of the drawbacks encountered with most of the methods of the prior art is that in these methods, the presence of an artificial biological or non-biological scaffold or carrier is needed on or within which cells are cultured to form a tooth primordium or tooth germ. A biological or non-biological scaffold or carrier is regarded as artificial if said scaffold or carrier is added or provided from the outside and is not formed by the cells used in the method of the invention during formation of cell aggregates. In the method of the present invention, the use or presence of such an artificial biological or non-biological scaffold or carrier is not needed. The method of the invention yields an artificial tooth primordium according to the invention without the use of any such artificial biological or non-biological scaffold or carrier which does not originate from the cells used in the production of said artificial tooth primordium. In a preferred embodiment, the method of the present invention is performed such that no artificial biological or non-biological scaffold is used in the formation of cell aggregates.

The method of the present invention is particular advantageous because artificial tooth primordial of the present invention can be produced starting from a single cell type, namely starting from isolated mesenchymal dental pulp cells. However, the generation of even more sophisticated artificial tooth primordial can be achieved if the method further comprises a step of co-culturing pre-condensed mesenchymal dental pulp cells with epithelial cells. The co-culturing is performed preferably under non-adherent culturing conditions. It appears to be particularly beneficial to culture the isolated mesenchymal dental pulp cells under non-adherent conditions for at least 48 hours to form pre-aggregated mesenchymal dental pulp cells, then to add the epithelial cells, and to co-culture the mixture of pre-aggregated mesenchymal dental pulp cells and epithelial cells under non-adherent conditions. Co-culturing may be performed for the periods of time defined and proposed above for non-adherent culturing of isolated mesenchymal dental pulp cells.

Preferably, the epithelial cells used in the method of the invention are primary epithelial cells, particularly preferred human primary epithelial cells. The primary epithelial cells may be derived from adult or non-embryonic tissue like e.g. skin tissue or gingival tissue. In a preferred embodiment the epithelial cells are keratinocytes, e.g. human keratinocytes, more preferably primary keratinocytes derived from non-embryonic tissues like e.g. skin or gingiva. Particularly preferred are human keratinocytes derived from gingiva e.g. from non-embryonic gingiva.

In the method of the invention with the co-culturing step, the epithelial cells are added for co-culture such that the number of mesenchymal dental pulp cells initially used to form pre-aggregated mesenchymal dental pulp cells is equal to or higher than the number of epithelial cells. Preferably, epithelial cells are added for co-culture in a relative amount of 1:1 to 1:10 related to the initial cell number of mesenchymal dental pulp cells, preferably in a relative amount of 1:2 to 1:8, more preferably in a relative amount of 1:3 to 1:5.

The method of the invention with the co-culturing step yields artificial tooth primordial of the invention, wherein the early cell aggregate forming the tooth primordium comprises a core formed of aggregated mesenchymal dental pulp cells and an outer layer formed of the epithelial cells. The long-term cultured aggregate may exhibit an invagination of the epithelial cells into the inner core of mesenchymal cells.

In the method of the invention, the mesenchymal dental pulp cells are cultured in adherent or non-adherent conditions with standard medium. There is no specialized culture medium necessary to induce proper cell aggregation under non-adherent conditions. The skilled person is well aware of suitable media. Typically standard DMEM is used with a certain content of fetal calf serum (FCS), preferably FCS is present in a concentration of 5% to 15%, more preferably in a concentration of 10% FCS. In case of co-culturing pre-aggregated mesenchymal dental pulp cells and epithelial cells under non-adherent conditions, the culture medium may comprise a certain amount of culture medium usually used in culturing the epithelial cells under adherent conditions.

The present invention is also directed to a transplant comprising or consisting of an artificial tooth primordium of the present invention or of a tissue or structure derived therefrom.

In another aspect of the invention a pharmaceutical composition is provided comprising an artificial tooth primordium of the present invention, a tissue or structure derived therefrom or a transplant of the invention and at least one pharmaceutically acceptable excipient.

The artificial tooth primordium of the invention, the transplant of the invention or the pharmaceutical composition of the invention may be used in the treatment of dental impairment and/or destruction or loss of teeth.

Since the method of the invention works with isolated mesenchymal dental pulp cells derived from non-embryonic sources, the method allows the production of artificial tooth primordia starting from cells derived from a particular donor or patient. Thus, it is possible to provide artificial tooth primordia that have been derived from the cells of the person to be treated with the artificial tooth primordium, pharmaceutical composition or transplant of the invention. Thus, it appears possible to provide a transplant that is mainly, substantially or completely derived from cells of the recipient of the transplant himself so that rejection reactions will be reduced to a minimum or will be completely absent.

The artificial tooth primordium of the invention may be used for the in vitro generation of tooth tissue or whole teeth.

The artificial tooth primordium of the invention, the transplant of the invention or the pharmaceutical composition of the invention may be used as a research tool that can be used in vitro and in vivo.

The artificial tooth primordium of the invention, the transplant of the invention or the pharmaceutical composition of the invention may be used in a method of screening for substances in vitro or in vivo, which modulate properties of tooth tissue.

The present invention additionally teaches a method for screening substances in vitro, which modulate properties of tooth tissue, comprising the steps of:
  providing a sample of an artificial tooth primordium of the invention or a cell aggregate prepared by a method of the invention or a tissue derived therefrom;
  dividing the respective sample into portions;
  incubating at least one portion with a substance to be screened; and
  comparing parameters measured for the treated portion with another portion that was not incubated with the substance to be screened.

In a preferred embodiment, the portion is subjected to a self-contained circulation system prior to incubating the portion with a substance to be screened.

Briefly, the inventive method makes the identification and analysis of substances possible, which exert an influence on tooth or tooth tissue via the artificial tooth primordium of the invention. The sample, which shall be understood to comprise a certain number of product subjects according to the invention, is divided into multiple portions. At least two subsets are provided; one is used for screening while the other one serves as negative control. Preferably, the number of screening parts exceeds the number of control parts. Usually, numerous portions are subjected to a high-throughput screening. The substances to be screened in the inventive method are not restricted anyway. In an embodiment of the invention, the substances are selected from the group of nucleic acids including RNAi, ribozymes, aptamers, antibodies, peptides, carbohydrates, polymers, small molecules having a molecular weight between 50 and 1.000 Da, and proteins, preferably antibodies, cytokines and lipocalins. These substances are often available in libraries. It is preferred to incubate a single compound within a distinct portion of the sample. However, it is also possible to investigate the cooperative effect of substances by incubating at least two substances within one portion. A further subset of subjects is simultaneously incubated in the absence of the substances. The incubation process depends on various parameters, e.g. the cell types and the sensitivity of detection, which optimization follows routine procedures known to those skilled in the art. The identification of effective substances in the meaning of the invention is preferably indirectly performed, e.g. by determining the expression patterns and/or the cell viability, which are altered. The determination may be performed at a specified moment and correlated to the signal strength at the beginning of the experiment and the negative control. Suitable tests are known to those skilled in the art or can be easily designed as a matter of routine.

Since the artificial tooth primordium of the invention can be regarded as an organ or a precursor of an organ or part thereof, it may be particularly beneficial to use a test system wherein the artificial tooth primordium can be prepared and/or cultured for a prolonged time under conditions which mimic natural perfusion. It appears particularly suitable to combine the method of the present invention and/or the artificial tooth primordium of the present invention in an assay system based on the self-contained organ-on-a-chip device described in the European patent application with the filing number EP 10 008 244 or in the PCT application with the publication number WO 2009/146911 A2.

The present invention provides for the first time an artificial tooth primordium and a method of producing the same, which is characterized by the lack of requirement of any artificial biological or non-biological scaffold or carrier, which is produced from adult cells so that no embryonic cells or tissues are needed and which requires only cells of one cell type, namely isolated mesenchymal dental pulp cells, or cells of two cell types, namely isolated mesenchymal dental pulp cells and keratinocytes.

The artificial tooth primordium of the present invention represents a functional inductive tooth germ which is capable of tooth organ development in vitro and in vivo. The resulting tooth organ is characterized by the verifiable presence of structures usually forming part of the developing tooth which are arranged in the physiological order of a tooth:

enamel, i.e. ameloblasts;
dentin;
dental pulp, incl. odontoblasts and undifferentiated dental pulp cells;
cementum, i.e. cementoblasts;
periodont; and
alveolar bone.

EXAMPLES

General Methods
Mesenchymal Dental Pulp Cell Isolation

Dental pulp cell isolation is performed according to a modified protocol from Gronthos et al. (A method to isolate and culture expand human dental pulp stem cells. Methods Mol Biol. 2011; 698:107-21).

1 Extracted third molars from patients after informed consent are collected in DMEM containing 10% FCS and penicillin and streptomycin (100 μg/ml each) and stored at 4° C. for not longer than 24 hours.
2 The biopsies are handled under sterile conditions throughout the whole procedure of cell extraction. Tooth crown and the root if present are wiped with 100% ethanol. To open the pulpal cavity, the tooth is split by mechanical cracking with a hammer
3 Pulp tissue is removed with forceps and placed into a PBS containing petri dish.
4 The tissue is then cut into small fragment which are then washed twice with PBS to remove debris and blood.
5 Afterwards a digestion step is performed with a collagenase (3 mg/ml)/dispase II (4 mg/ml) enzyme mix for 2 h at 37° C.
6 The digested solution is the filtered through a 70 μm cell strainer and washed twice with PBS by centrifugation (400×g for 5 min). The remaining cell pellet is resuspended in DMEM w/10% FCS and penicillin and streptomycin (100 μg/ml each).

Cell Culture

Culture and expansion of mesenchymal dental pulp cells is achieved by maintaining cells in monolayer culture onto culture flask surfaces for adherent cells in DMEM w/10% FCS and penicillin and streptomycin (100 μg/ml each) under standard culture conditions (5% CO2, 37° C.). The adherent fibroblast-like mesenchymal cells are grown to 90% confluency and then passaged.

Aggregation/Condensation Process for Formation of Artificial Tooth Primordium

For culture under non-adherent conditions, mesenchymal dental pulp cells of approx. $2^{nd}$ to $8^{th}$ passage are passaged two days prior to use, were harvested and resuspended in DMEM+10% FCS to yield up in a single cell suspension of 106 cells per ml. The cell suspension (1 ml per well) was given to 24 well low attachment plate (Ultra Low Cluster Plate, Corning, Germany). In contrast to the negatively charged, hydrophilic surface of standard tissue culture dishes the ultra low attachment plates possess a neutral, hydrophilic hydrogel coated surface that greatly minimizes the binding of attachment proteins. By using this specialized culture dishes the mesenchymal dental pulp cells do not settle down through cell adhesion as in micromass culture. The formation of a 2D monolayer culture was prevented and the cells retained a round shape under this suspension culture maintaining non-adherent conditions. Furthermore, in contrast to methods relying on an external scaffold or carrier, the low attachment culture system provides the opportunity for free cell movement and cell cell interaction during an initial condensation process. Condensation process starts shortly after seeding and is observed macroscopically by cells forming aggregates. To ensure constant culture conditions medium was changed regularly every 3 days.

Co-Culture

If co-culture of mesenchymal dental pulp cells and cells of epithelial origin (skin derived or gingival keratinocytes) is intended, the condensates produced described by the method above are transferred at day 2 to 5 in a composite medium appropriate for both cell types (e.g. standard DMEM (w/FCS) and Keratinocyte Culture Medium; 1:1). A single cell suspension of epithelial cells in a ratio of 1:4 related to the initial cell number used for mesenchymal condensation was added and the resulting mixture was cultured under non-adherent conditions. To ensure constant culture conditions medium was changed regularly every 3 days.

Results

Figure 1:
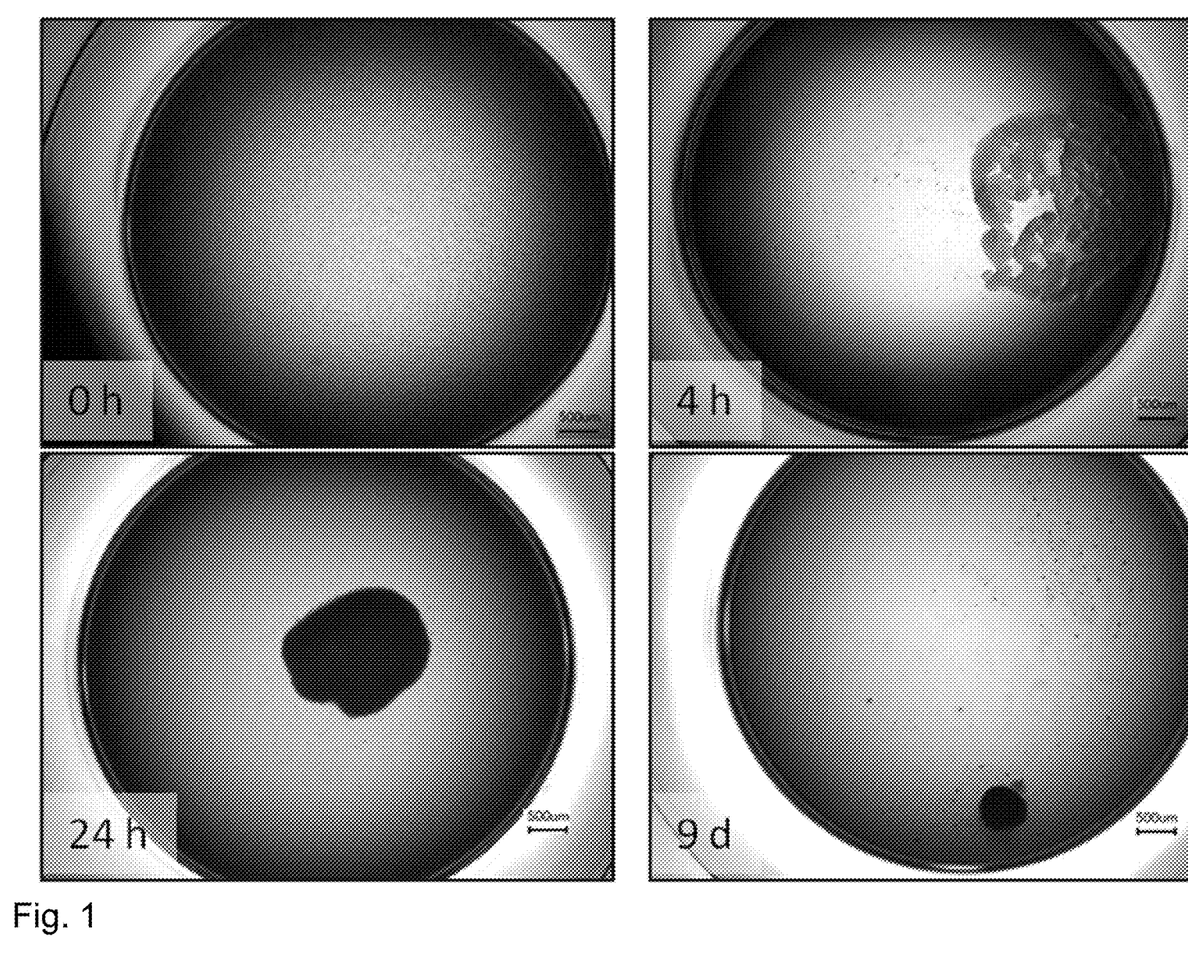
FIG. 1 shows three-dimensional low-attachment culture of human mesenchymal dental pulp cells; scale bars: 500 μm.

In order to expand human dental pulp cells (hDPCs) used for preparation of an artificial tooth primordium in vitro, the isolated cells were cultured for at least 2 passages in monolayer. As described cells adopt a fibroblastic morphology and express MSC surface markers (CD90, CD73, CD44, CD29 and HLA I (data not shown). To accomplish an induction of cellular arrangement and differentiation, hDPCs are cultured in a three-dimensional manner. The idea of the low-attachment culture technique described above is to avoid cell attachment to the culture dish surface and to allow self-organization mediated by cell mobility. Therefore, human mesenchymal dental pulp cells (hDPCs) were seeded in a density of $1\times10^6$ cells/ml in low-attachment culture plates in normal DMEM with 10% FCS and were cultured at standard cell culture conditions. Dental pulp cells arrange freely to each other and condense to a three-dimensional cell aggregate. Condensation begins quickly after seeding. Already after 4 hours most of the cells are associated to form a cell aggregate. Within 24 hours after seeding, the cell aggregate further condenses (FIG. 1). This cell aggregate remains viable for a prolonged period of time and further develops and differentiates into an artificial tooth primordium of the present invention with an average of 0.3 mm in diameter.

Figure 2:
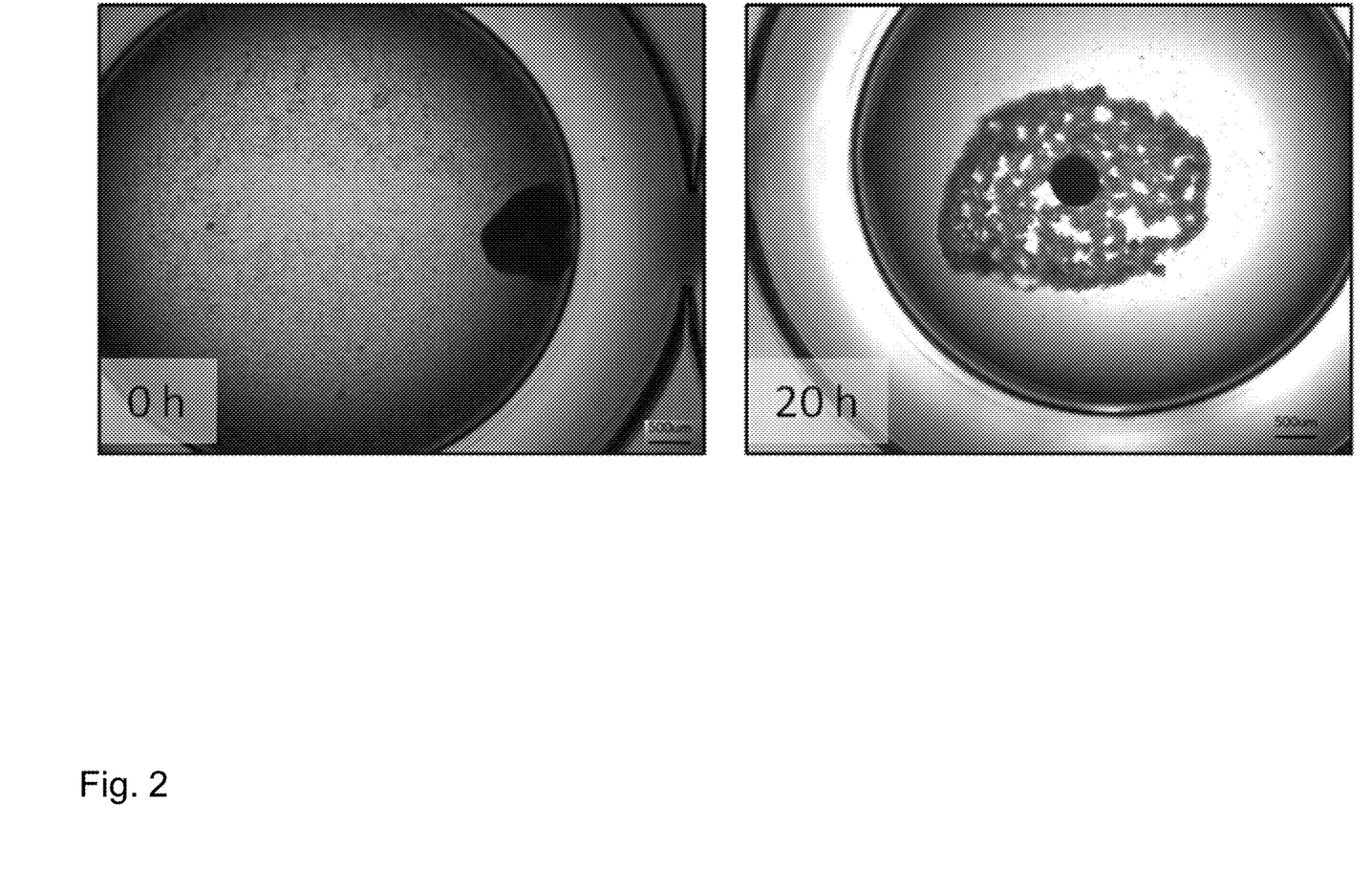
FIG. 2 shows human dental pulp cells in co-culture with keratinocytes; scale bars: 500 μm. Given time points indicate hours after addition of keratinocytes.

To assess whether these mesenchymal condensated are capable of interaction with human gingival keratinocytes and whether an ameloblastic differentiation can be induced by these condensates hDPC condensates and keratinocytes were co-cultured in the three-dimensional low-attachment system. Here, primary human keratinocytes isolated from gingiva were added as single cell suspension of epithelial cells in a ratio of 1:4 related to the initial cell number used for mesenchymal condensation to 48 h old mesenchymal hDPC aggregates. The resulting mixture was then cultured under non-adherent conditions. Keratinocytes arrange around the three-dimensional mesenchymal aggregate. The gingival keratinocytes are attracted and rapidly assemble around the condensated (FIG. 2).

Figure 3:
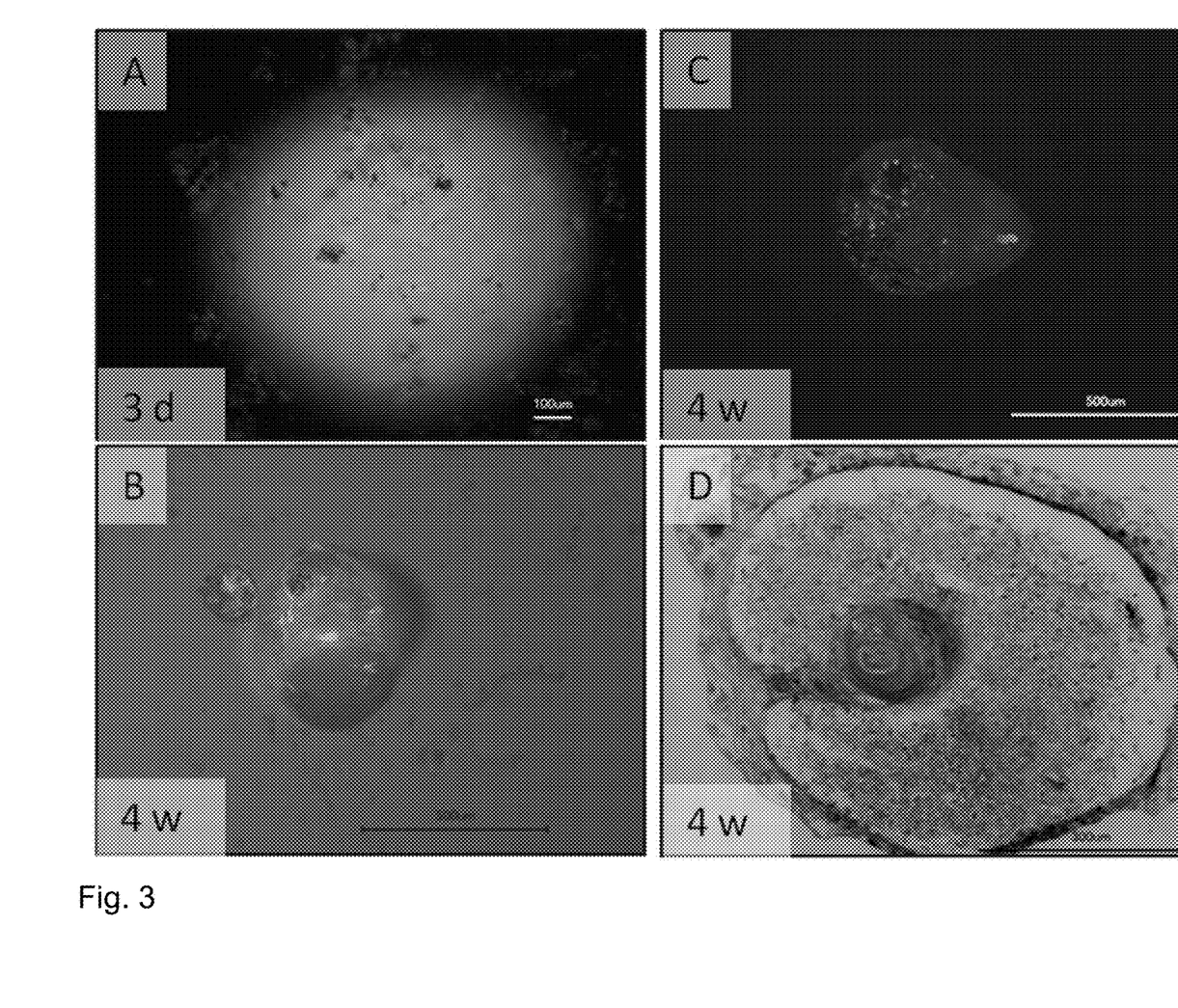
FIG. 3 shows self-assembled cell type compartmentalization of the primordium described by the invented method; scale bars: A: 100 μm B, C: 500 μm D: 300 μm. Given time points indicate time after addition of keratinocytes.

During tooth development a strong interaction between the mesenchymal and epithelial tissues is observed leading to proliferation and invagination. In order to trace the interplay between these two cell types induced by the culture method described by the invention, the used cells were fluorescently labelled. Constitutively eGFP-expressing hDPCs were seeded in a density of $1\times10^6$ cells/ml in low-attachment culture plates and cultured as described above for 24 hours. Afterwards primary human keratinocytes tracked with CellTracker™ Red CMTPX (Molecular Probes®) were added as single cell suspension of epithelial cells in a ratio of 1:4 related to the initial cell number used for mesenchymal condensation and the resulting mixture was cultured under non-adherent conditions. After three days, keratinocytes are attached to the surface of the mesenchymal aggregate (FIG. 3A). Four weeks of co-culture lead to a completely "interwoven" structure within the self-assembled condensate. At this point in time keratinocytes can be detected underneath a layer of hDPCs within the constructed organoid by fluorescence microscopy (FIG. 3B). This observation is further evidenced by fluorescent microscopic analysis of cryo-sections (8 μm thickness) (FIG. 3C). Combined hematoxylin/eosin staining further elucidates the structural compartmentalization of the artificial tooth primordium (FIG. 3D). Keratinocytes which appear distinctly pink due to expression of acidic proteins (e.g. Cytokeratin 15 and 18) invaginated at one site of the three-dimensional condensate. The band of epithelial tissue which connects the invaginated cells with the surrounding epithelium resembles the dental lamina during tooth development. The mesenchyme is clearly separated from the outer epithelium by a connective tissue-like layer and completely surrounds the invaginated structure.

Figure 4:
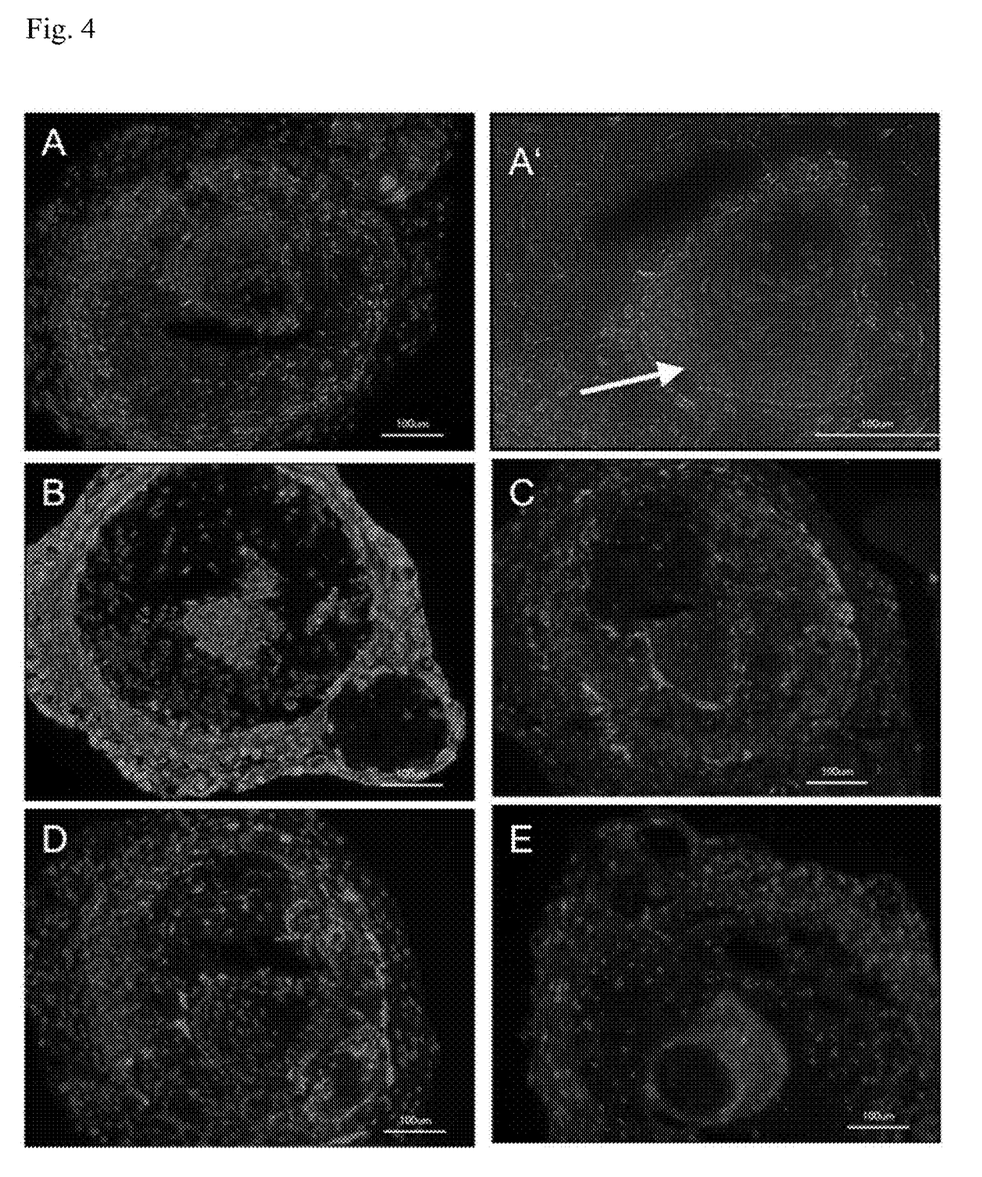
FIG. 4 shows expression of intra- and extracellular molecules to characterize the constructed tooth primordium.

Artificial tooth primordia prepared by the method of the invention were subjected to comprehensive immunohistological analysis after 8 weeks of culture. The constructed organoids were characterized regarding the expression of intra- and extracellular molecules. For detection of the respective proteins, primary antibodies were used against Vimentin, Cytokeratin 15, Collagen type I, Collagen type IV and Ki67. Secondary antibodies were coupled with Alexa Fluor® 594 (red) for detection under fluorescence microscope (FIG. 4). All sections were counterstained with Hoechst33258 (blue). Vimentin (FIG. 4A/A') and Cytokeratin 15 (FIG. 4B) clearly mark the areas of mesenchyme and epithelium respectively. Collagen type I (FIG. 4C) is exclusively expressed in the mesenchymal part of the aggregate as part of extracellular matrix. Note that Collagen type I is a major component of dentin. Collagen type IV (FIG. 4D) is highly expressed at the interface of the two cell types mimicking a basal lamina. Proliferative activity is exclusively detected in the epithelial cell layers as indicated by the presence of Ki67 (FIG. 4E). Note the columnar arrangement of the invaginated epithelium (FIG. 4A'; see arrow). In vivo inner enamel epithelium also arranges in a columnar layer during cap stage and gives then rise to pre-ameloblasts and ameloblasts.

The invention claimed is:

1. A method of preparing an artificial tooth primordium in vitro, comprising the steps:
providing isolated mesenchymal dental pulp cells in the form of a single-cell suspension;
subsequently culturing the single-cell suspension of mesenchymal dental pulp cells under non-adherent conditions in ultra low attachment plates with a neutral hydrophilic hydrogel coated surface for at least two days to form a cell aggregate having a substantially spherical shape and a diameter of 0.3 mm to 2 mm, wherein no artificial biological or non-biological scaffold is used in the formation of the cell aggregate;

transferring the mesenchymal dental pulp cell aggregates to a composite culture medium appropriate for both mesenchymal dental pulp cells and epithelial cells;

adding a single cell suspension of epithelial cells in a ratio of 1:4 related to the initial cell number used for mesenchymal aggregate formation;

culturing the cell mixture in ultra low attachment plates under non-adherent conditions;

and changing the culture medium every 3 days.

2. The method of claim 1, wherein the mesenchymal dental pulp cells comprise or consist of primary adult mesenchymal dental pulp cells.

3. The method of claim 1, wherein the mesenchymal dental pulp cells are derived from dental pulp tissue of a tooth.

4. The method of claim 1, wherein the mesenchymal dental pulp cells are subjected to non-adherent culture conditions at a concentration of $5 \times 10^4$ to $5 \times 10^7$ per ml.

5. The method of claim 1, wherein the mesenchymal dental pulp cells are cultured under non-adherent conditions at least until a cell aggregate having a substantially spherical shape and a diameter of 0.5 mm to 1.5 mm is formed.

6. The method of claim 1, wherein the mesenchymal dental pulp cells are cultured under non-adherent conditions at least until the cell aggregate formed exhibits upregulated expression of Bone Morphogenetic Protein 4 (BMP4), Hepatocyte Growth Factor (HGF), Paired Box Gene 9 (PAX9), Msh Homeobox 1 (MSX1), Collagen type I, Dentin Sialophosphoprotein (DSPP) and/or predentin compared to isolated mesenchymal dental pulp cells immediately prior to subjecting to non-adherent culturing conditions.

7. The method of claim 1, wherein the epithelial cells are keratinocytes.

8. The method of claim 3, wherein the mesenchymal dental pulp cells are derived from dental pulp tissue of a third molar.

9. The method of claim 7, wherein the keratinocytes are derived from skin or gingiva.

* * * * *